United States Patent
Coscia

(10) Patent No.: US 11,815,211 B2
(45) Date of Patent: Nov. 14, 2023

(54) ASEPTIC COUPLING ASSEMBLY AND METHOD OF ASEPTIC COUPLING

(71) Applicant: ENTEGRIS, INC., Billerica, MA (US)

(72) Inventor: Nicholas Coscia, Lexington, MA (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 17/827,423

(22) Filed: May 27, 2022

(65) Prior Publication Data
US 2022/0381384 A1    Dec. 1, 2022

Related U.S. Application Data

(60) Provisional application No. 63/194,081, filed on May 27, 2021.

(51) Int. Cl.
*F16L 37/098*    (2006.01)
*F16L 37/30*    (2006.01)
(Continued)

(52) U.S. Cl.
CPC ........... *F16L 37/098* (2013.01); *A61M 39/18* (2013.01); *F16L 37/30* (2013.01); *A61M 2039/1027* (2013.01); *F16L 2201/44* (2013.01)

(58) Field of Classification Search
CPC ..... F16L 37/098; F16L 2201/44; F16L 37/30; A61M 39/18; A61M 2039/1027
See application file for complete search history.

(56) References Cited

U.S. PATENT DOCUMENTS 3,865,411 A * 2/1975 Rowe ................. F16L 23/22
                                                                285/915
4,418,945 A * 12/1983 Kellogg ............... A61M 39/14
                                                                 285/70
(Continued)

FOREIGN PATENT DOCUMENTS

CA            2961688 A1 * 9/2017 ......... A61M 39/1011
DE    102013214068 A1 * 1/2015 ............ A61M 39/18
(Continued)

OTHER PUBLICATIONS

"Adtech" ("Fluoropolymer properties: What makes them so unique?" by "Adtech", NPL publicly available since at least Aug. 2020; https://adtech.co.uk/about/news/fluoropolymer-properties). (Year: 2020).*
(Continued)

*Primary Examiner* — David Colon-Morales

(57) ABSTRACT

An aseptic low-temperature coupling assembly includes a first connector, a second connector, and a gasket disposed in the first or the second connector. The first and second connectors include a first retaining feature and a second retaining feature configured to couple together the first and the second connectors and align openings in the first and second connectors. The gasket is formed to have no substantial deformation after being cooled to at least −50° C. then heated to ambient temperature. A method of aseptically connecting a low-temperature fluid storage container includes coupling a first connector to a second connector via first retaining features and second retaining features of the connectors. The coupling compresses a gasket between the first connector and the second connector and aligns an opening in the first connector with an opening in the second connector.

17 Claims, 7 Drawing Sheets

(51) Int. Cl.
*A61M 39/18* (2006.01)
*A61M 39/10* (2006.01)

(56) References Cited

U.S. PATENT DOCUMENTS

| | | | | |
|---|---|---|---|---|
| RE32,056 E | * | 12/1985 | Granzow | B29C 65/58 |
| | | | | 156/304.6 |
| 9,335,000 B2 | * | 5/2016 | Selker | B01D 35/28 |
| 9,364,653 B2 | * | 6/2016 | Williams | F16L 37/30 |
| 9,770,581 B2 | * | 9/2017 | Gerst | A61M 39/1011 |
| 10,267,443 B2 | * | 4/2019 | Blake | A61M 39/18 |
| 2009/0015005 A1 | | 1/2009 | Johnson | |
| 2013/0207380 A1 | * | 8/2013 | Williams | F16L 37/30 |
| | | | | 29/426.1 |
| 2019/0083772 A1 | | 3/2019 | Miltenyi et al. | |
| 2021/0062946 A1 | * | 3/2021 | Gerst | F16L 55/105 |
| 2021/0095802 A1 | | 4/2021 | Andrews et al. | |

FOREIGN PATENT DOCUMENTS

| | | |
|---|---|---|
| EP | 2665502 B1 | 3/2020 |
| KR | 20160146828 A | 12/2016 |
| WO | WO-8402321 A1 * | 6/1984 |

OTHER PUBLICATIONS

"Custom Gasket" ("Selection Guide to Rubber Gasket Materials" by "Custom Gasket", NPL publicly available since at least May 3, 2021; https://www.customgasketmfg.com/blog/rubber-gasket-materials/) (Year: 2021).*

"Polymax" ("What is the best low temperature O-ring" by "Polymax", NPL publicly available since at least Oct. 2018; https://www.polymax.co.uk/blog/what-is-the-best-low-temperature-o-ring/) (Year: 2018).*

"Associated Gaskets" ("Gylon 3504 Gasket Material" by "Associated Gaskets", NPL publicly available since at least Apr. 2019, https://agaus.com.au/product/gylon-3504-gasket-material/). (Year: 2019).*

* cited by examiner

ASEPTIC COUPLING ASSEMBLY AND METHOD OF ASEPTIC COUPLING

FIELD

This disclosure is directed to aseptic coupling and coupling assemblies used in aseptically coupling of a low-temperature storage container.

BACKGROUND

Chemical and/or biological processes can utilize or produce process materials that are stored within storage containers, such as bags, containing pharmaceutical or biological fluids, bioprocess bags, and the like. Tubing or other types of coupling may be utilized to supply the process material and/or reactants into to the storage container. The process materials may need to be frozen or otherwise kept at low temperatures within the storage container. Tubing or other types of coupling may then be utilized to remove the process material from the storage container.

SUMMARY

In an embodiment, an aseptic low-temperature coupling assembly includes a first connector, a second connector, and a gasket disposed in one of the first connector and the second connector. The first connector and the second connector each include a fluid passage with an opening. Each of the first connector and the second connector also include a first retaining feature and a second retaining feature disposed on opposite sides of the opening of its fluid passage. The first retaining feature and the second retaining feature have complementary shapes.

The first connector and the second connector are configured to be coupled together by the first and second retaining features of the first connector engaging with the first and second retaining features of the second connector, in which the opening of the first fluid passage aligns with the opening of the second fluid passage. The gasket is formed to have no substantial deformation after being cooled to at least −50° C. then heated to ambient temperature.

In an embodiment, a method of aseptically connecting a low-temperature fluid storage container includes coupling a first connector to a second connector via first retaining features and second retaining features. Each of the first connector and the second connector includes a fluid passage that extends through the respective connector.

The coupling of the first connector to the second connector includes: engaging the first retaining features with the second retaining features, compressing a gasket between the first connector and the second connector, and aligning openings of the first and second fluid passages. Each of the first connector and the second connector includes one of the first retaining features and one of the second retaining features disposed on opposite sides of the opening in the respective one of the first connector and the second connector. The gasket is disposed in one of the first connector and the second connector. The first gasket is formed to have no substantial deformation after being heated to ambient temperature from a temperature of at least −50° C.

DRAWINGS

Like numbers represent like features.

DETAILED DESCRIPTION

Figure 1:
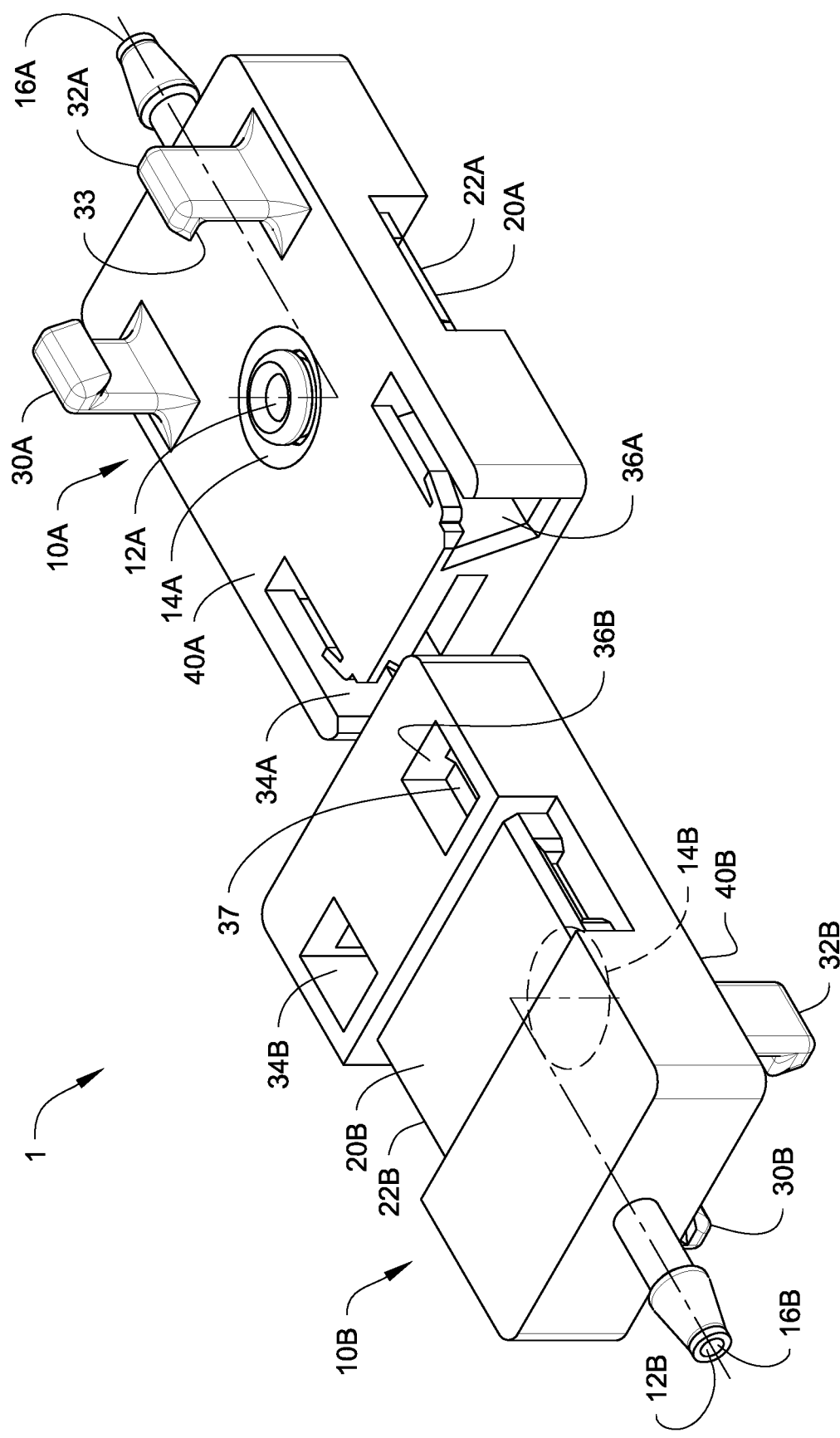
FIG. 1 is a front perspective view of an embodiment of an aseptic low-temperature coupling assembly.

FIG. 1 is a perspective view of an embodiment of an aseptic low-temperature coupling assembly 1. The coupling assembly 1 includes a first connector 10A and a second connector 10B that are configured to couple together to form a sealed fluid connection. The first connector 10A includes a first fluid passage 12A that extends through the first connector 10A. The second connector 10B includes a second fluid passage 12B that extends through the second connector 10B. The first fluid passage 12A and the second fluid passage 12B are generally indicated with dashed lines in FIG. 1. When the first connector 10A is coupled to the second connector 10B, the first fluid passage 12A and the second fluid passage 12B are joined to form a sealed fluid connection that extends through the coupled connectors 10A, 10B.

The first fluid passage 12A includes an opening 14A disposed in the external surface of the first connector 10A. For example, the opening 14A is disposed in the upper surface 40A of the first connector 10A that faces the second connector 10B when coupled. The first fluid passage 12A also include a second opening 16A at the opposite end of the first fluid passage 12A. In an embodiment, the second opening 16A may be the inlet of the first connector 10A and the first opening 14A may be the outlet of the first connector 10A.

The second fluid passage 12B includes an opening 14B disposed in the external surface of the second connector 10B. For example, the opening 14B is disposed in a lower surface 40B of the second connector 10B (shown in FIG. 3) that faces the first connector 10A when coupled. The second fluid passage 12B also include a second opening 16B at the opposite end of the second fluid passage 12B. For example, the first opening 14B can be the inlet of the second fluid passage 12B and the second connector 10B and the second opening 16B can be the outlet of the second fluid passage 12B and the second connector 10B. In the coupled connectors 10A, 10B, opening 16A can be an inlet of the assembly 1 while the opening 16B can be the outlet of the assembly 1. The connection of the passages 12A, 12B in the coupled connector is discussed in more detail below.

The first connector 10A and the second connector 10B include retaining features 30A, 30B, 32A, 32B, 34A, 34B, 36A, 36B (retaining feature 36A is obscured in FIG. 1) that are used to couple the connectors 10A, 10B together. The retaining features include first retaining features 30A, 32A, 30B, 32B (one of the first retaining features 30B is obscured in FIG. 1) and corresponding second retaining features 34A, 36A, 34B, 36B. Each connector 10A, 10B has a first retaining features 30A, 30B and a second retaining feature 34A, 34B disposed on an opposite sides of the opening 14A, 14B of their respective fluid passage 12A, 12B.

The first and second retaining features 30A, 32A, 34A, 36A of the first connector 10A engage with the first and second retaining features 30B, 32B, 34B, 36B of the second connector 10B to couple together the first connector 10A and the second connector 10B. In the first connector 10A and the second connector 10B, first retaining feature 30A/30B, 32A/32B and second retaining feature 34A/34B, 36A/36B have a corresponding shape. A first retaining feature 30A and a second retaining feature 34A of the first connector 10A have a corresponding shape. For example, a first retaining feature 30A has a shape that would be capable of engaging with the second retaining feature 34B. As shown in FIG. 1, the first connector 10A can have the same number and configuration of retaining features as the second connector 10B. For example, the first connector 10A and the second connector 10B can have the same general shape.

Figure 2:
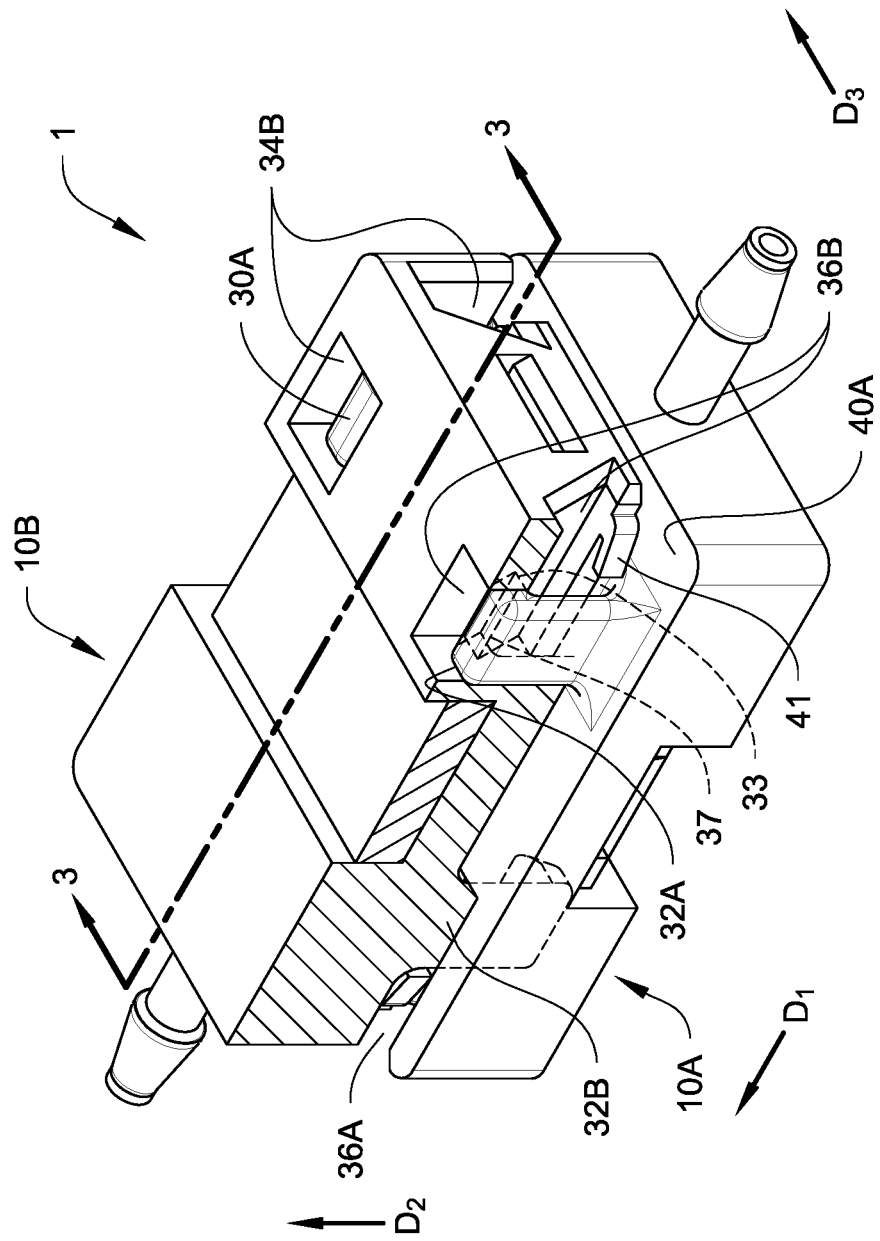
FIG. 2 is a rear perspective view of a partial section of the aseptic low-temperature coupling assembly of FIG. 1, according to an embodiment.

The connectors 10A, 10B are coupled together (e.g., as shown in FIG. 2) by the first retaining features 30A, 32A, 30B, 32B engaging with the second retaining features 34A, 36A, 34B, 36B. The first retaining features 30A, 32A of the first connector 10A engage corresponding second retaining features 34B, 36B of the second connector 10B, and the first retaining features 30B, 32B of the second connector 10B engage corresponding second retaining features 34A, 36A of the first connector 10A. For example, first retaining feature 30A engages with second retaining feature 34B, first retaining feature 32A engages with the second retaining feature 36B, first retaining feature 30B engages with second retaining feature 34A, and first retaining feature 32B engages with the second retaining feature 36A.

The connectors 10A, 10B are genderless connectors. Each of the connectors 10A, 10B has at least one of the first retaining features 30A, 30B, 32A, 32B and at least one of the second retaining features 34A, 34B, 36A, 36B. In the illustrated embodiment, each of the connectors 10A, 10B includes two of the first retaining features 30A/30B, 32A/32B and two of the second retaining features 34A/34B, 36A/36B. In an embodiment, the first connector 10A and the second connector 10B may each have one first retaining feature 30A, 30B, 32A, 32B and one second retaining feature 34A, 34B, 36A, 36B.

The first connector 10A and the second connector 10B each include a plurality of the first retaining features 30A, 32A and a plurality of the second retaining features 34A, 36A. The first connector 10A and the second connector 10B can each include two of the first retaining features 30A/30B, 32A/32B and two of the second retaining features 34A/34B, 36A/36B. In an embodiment, the first connector 10A may include one or more of the first retaining features 30A, 32A and one or more of the second retaining features 34A, 36A. In an embodiment, the second connector 10B include at least one first retaining feature 30B, 32B and at least one second retaining feature 34B, 36B. Accordingly, each of the first connector 10A and the second connector 10B is a genderless connector as it includes both a male retaining feature (e.g., first retaining feature 30A/30B, 32A/32B) and a female retaining feature (e.g., second retaining feature 34A/34B, 36A/36B).

The first retaining features 30A, 30B, 32A, 32B can be any suitable structure for forming a mechanical connector with the complementary second retaining features 34A, 34B, 36A, 36B to form a snap-fit, pressure-fit, or the like. For example, each first retaining feature(s) 30A, 32A of the first connector 10A can be any suitable structure for forming a mechanical connector with a respective complementary retaining feature 34B, 36B of the second connector 10B. The retaining features can include, for example, slots, tabs, flanges, detents, hooks, or any other suitable structures for mechanical engagement with other structures. In the embodiment of FIG. 1, the first retaining features 30A, 30B, 32A, 32B include retaining projections.

Second retaining features 34A, 34B, 36A, 36B can be any suitable structure for forming a mechanical connector with the complementary first retaining features 30A, 30B, 32A, 32B to form a snap-fit, pressure-fit, or the like. For example, each first retaining feature(s) 30A, 32A of the first connector 10A can be any suitable structure for forming a mechanical connector with a respective complementary retaining feature 34B, 36B of the second connector 10B. The retaining features can include, for example, slots, tabs, flanges, detents, hooks, or any other suitable structures for mechanical engagement with other structures. In the embodiment of FIG. 1, the second retaining features 34A, 34B, 36A, 36B include retaining slots. The retaining slot(s) can extend all the way through their respective connector 10A, 10B.

The aseptic low-temperature coupling assembly 1 can include a pair of removable films 20A, 20B that can seal the first and second fluid passages 12A, 12B from the ambient environment prior to the coupling of the connectors 10A, 10B. The removable films 20A, 20B respectively cover and seal the openings of the respective first and second fluid passages 12A, 12B. For example, the first pull film 20A covers and seals the opening 14A of the first fluid passage 12A, and the second pull film 20B covers and seals the opening 14B of the second fluid passage 12B. The removable films 20A, 20B are configured to maintain the fluid passages 12A, 12B as aseptic prior to the coupling of the connectors 10A, 10B. For example, each pull film 20A, 20B prevents containments in the air (e.g., as dust, moisture, etc.) from entering the opening 14A, 14B of its respective fluid passage 12A, 12B that is used to fluidly connect the fluid passages 12A, 12B in the coupled connectors 12A, 12B. The opposite opening of each fluid passage 12A, 12B (e.g., opening 16A of the first fluid passage 12A, opening 16B of the second fluid passage 12B) can be attached to a sealed connection (e.g., tubing, a bioprocessing bag, etc.). The removable films 20A, 20B are removed once the connectors 10A and 10B have been connected. For example, the removable films 20A, 20B are removed after being compressed between the connected connectors 10A, 10B.

In an embodiment, the removable films 20A, 20B are pull films configured to be removed by being pulled off of the connectors 10A, 10B. The coupling compresses the pair of removable films 20A, 20B between the two connectors 10A, 10B. The assembly of the aseptic low-temperature coupling assembly 1 can include pulling on the compressed removable films 20A, 20B to remove the removable films 20A, 20B from the coupled connectors 10A, 10B. In an embodiment, the compressed removable films 20A, 20B are configured to be pulled on and removed simultaneously from between the coupled connectors 10A, 10B. For example, the connectors 10A, 10B compress removable films 20A, 20B along a first direction (e.g., compressed along direction $D_2$ in FIG. 2), and the compressed removable films 20A, 20B are removed by being pulled in a second direction that is transverse to the first direction (e.g., pulled in direction $D_3$ in FIG. 2).

The removable films 20A, 20B are attached to the connectors 10A, 10B in a manner that allows for the removable films 20A, 20B when compressed between the coupled connectors 10A, 10B to be simultaneously pulled on and simultaneously removed from between the connectors 10A, 10B. The attachment of removable films 20A, 20B allows for a user to simultaneously grasp both of the removable films 20A, 20B so that the removable films 20A, 20B can be simultaneously pulled on and removed. The configuration of the removable films 20A, 20B allows for a user, by hand, to grasp both removable films 10A, 10B and pull them in a transverse direction to the direction of compression (e.g., in transverse direction $D_3$). For example, the removable films 20A, 20B can each include an end 22A, 22B configured to be pulled away from their respective connector 10A, 10B. The ends 22A, 22B is configured to pull away from their connector 10A, 10B so form the entire removable films 20A, 20B into a planar shape, which can then be pulled in the single traverse direction to remove the compressed removable films 20A, 20B from between the two connectors 10A, 10B. The removable films 20A, 20B become entirely detached from connectors 10A, 10B once removed.

This configuration for the connectors 10A, 10B and removable films 20A, 20B allows for the opening of the first fluid passage 12A and the opening of the second fluid passage 12B remain sealed by their respective film 20A, 20B until the assembly 1 is assembled. This advantageously keeps the fluid passages 12A, 12B aseptic until they can form a sealed connection to each other in the coupled connectors 10A, 10B.

FIG. 2 illustrates a prospective partial sectional view of the assembled aseptic low-temperature coupling assembly 1, according to an embodiment. A sectional view of the second connector 10B is shown in FIG. 2. Obscured features are shown in dashed lines in FIG. 2.

As shown in illustrated embodiment, the first retaining features can include a first retaining projection and a second retaining projection, and the second retaining features can include a first retaining slot and a second retaining slot. For example, first retaining feature 32A is a first retaining projection that engages with second retaining feature 36B that is a first retaining slot, and first retaining feature 32B is a second retaining projection that engages with second retaining features 36A that is a second retaining slot. In an embodiment, the other first retaining features 30A, 30B, 32B may engage with their respective second retaining feature 34A, 34B, 36A in a similar manner to the first retaining feature 32A and second retaining feature 36B shown in FIG. 2.

The retaining projection 32A extends from an upper surface 40A of the connector 10A. The upper surface 40A of the connector 10A faces the opposite connector 10B when the connectors 10A, 10B are connected. In the embodiment shown on FIGS. 2 and 3, a tab 33 on the retaining projection 32A forms a snap fit over a lip 37 of the retaining slot 36B. The retaining projection 32A engages with the retaining slot 36B by being inserted into the retaining slot 36B in a first direction $D_1$, then moving the retaining projection 32A in a second direction. The movement in the first direction $D_1$ aligns the retaining projection 32A with the lip 37 within the retaining slot 36B (e.g., aligns the retaining projection 32A with the lip 37 in the horizontal direction $D_1$), and the movement in the second direction $D_2$ snap fits the tab 33 over and onto the lip 37. For example, the movement in the first direction $D_1$ generally moves the connectors 10A, 10B perpendicular to each other, and the movement in the second direction $D_2$ moves the connectors 10A, 10B closer together.

The retaining slot 36B can also include a bendable restraining member 41 that prevents removal of the retaining projection 32A once inserted into the retaining slot 36B. The insertion of the retaining projection 32A into the retaining slot 36B in the first direction $D_1$ bends the restraining member 41. For example, after the retaining projection 32A is full inserted into retaining slot 36B in the first direction $D_1$, the restraining member 41 limits the movement of the retaining projection 32A along the first direction $D_1$ (e.g., limits movement of the retaining projection 32A in the opposite direction). The restraining member 41 is configured to allow the pertaining projection 32A to be moved in the second direction $D_2$ to snap fit the tab 33 with the lip 37.

Figure 3:
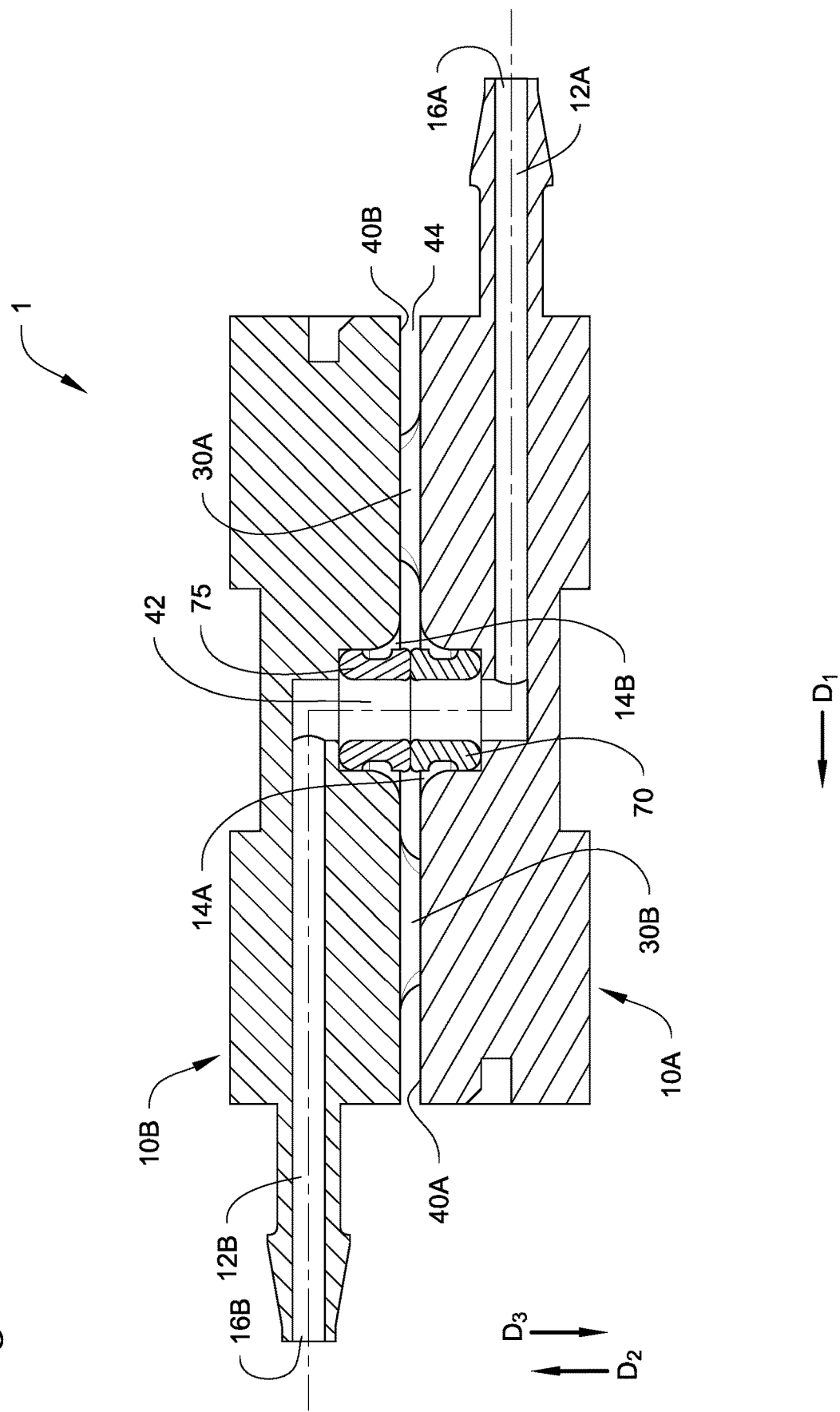
FIG. 3 is a sectional view of the aseptic low-temperature coupling assembly as indicated in FIG. 2, according to an embodiment.

FIG. 3 shows a sectional view of the assembled aseptic low-temperature coupling assembly 1, according to an embodiment. The sectional view of FIG. 3 is indicated in FIG. 2. FIG. 3 shows the connecting of the first fluid passage 12A of the first connector 10A with the second fluid passage 12B of the second connector 10B in the assembled aseptic low-temperature coupling assembly 1. As shown in FIG. 3, when coupled together, the first connector 10A can be configured to only directly contact the second connector 10B via their retaining features. For example, a gap 44 is provided between main opposing surfaces 40A, 40B of the connectors 10A, 10B (e.g., between the upper surface 40A of the first connector 10A and the lower surface 40B of the second connector 10B).

The first fluid passage 12A includes the opening 14A disposed in the external surface of the first connector 10A. For example, as shown in FIG. 3, the opening 14A is disposed in the upper surface 40A of the first connector 10A that faces the second connector 10B when coupled. The first fluid passage 12A also include a second opening 16A at the opposite end of the first fluid passage 12A. For example, the first opening 14A can be configured to be an inlet of the first connector 10A and the second opening 16A can be configured to be an outlet of the first connector 10A.

The second fluid passage 12B includes an opening 14B disposed in the external surface of the second connector 10B. For example, as shown in FIG. 3, the opening 14B is disposed in a lower surface 40B of the second connector 10B that faces the first connector 10A when coupled. The second fluid passage 12B also include a second opening 16B at the opposite end of the second fluid passage 12B. For example, the first opening 14B can be the inlet of the second fluid passage 12B and the second connector 10B and the second opening 16B can be the outlet of the second fluid passage 12B and the second connector 10B. In the coupled connectors 10A, 10B, opening 16A can be an inlet of the assembly 1 while the opening 16B can be the outlet of the assembly 1.

As shown in FIG. 3, the opening 14A of the first fluid passage 12A is aligned with the opening 14B of the second fluid passage 12B in the coupled connectors 10A, 10B. The openings 14A, 14B aligned by overlapping at least partially. As shown in FIG. 3, the openings being aligned and overlapping with respect to the second direction $D_2$ (e.g., in the vertical direction).

The assembly aseptic low-temperature coupling assembly 1 includes a first gasket 70 and a second gasket 75. The first gasket 70 is obscured in FIG. 1 as it is covered by the first pull film 20A. Prior to coupling, the pull film 20A (shown in FIG. 1) is disposed over and seals the first gasket 70 and the first fluid passage 12A. For example, the pull film 20A covers and forms a seal over the opening 14A and the first gasket 70 disposed in the opening 14A of the first fluid passage 12A. In a similar manner, pull film 20B (shown in FIG. 1) is disposed over and seals the second gasket 75 and the second fluid passage 12B. As discussed above, the coupling of the connectors 10A, 10B compresses the removable films 20A, 20B between the connectors 10A, 10B. More specifically, the removable films 20A, 20B are compressed between the two gaskets 70, 75. The coupling of the connectors 10A, 10B pinches the removable films 20A, 20B between the two gaskets 70, 75. For example, the removable films 20A, 20B are pinched between the top of the first gasket 70 and the bottom of the second gasket 75.

As shown in FIG. 3, the first gasket 70 is disposed in the first connector 10A and the second gasket 75 is disposed in the second connector 10B. The first gasket 70 is disposed in the first fluid passage 12A of the first connector 10A. The second gasket 75 is disposed in the second fluid passage 12B of the second connector 10B. More particularly, the first gasket 70 is disposed in an end portion of the first fluid passage 12A and extends out through the opening 14A of the first fluid passage 12A. The second gasket 75 is disposed in an end portion of the second fluid passage 12B and extends out through the opening 14B of the second fluid passage 12B. As shown in FIG. 3, the first gasket 70 and the second gasket 75 are each disposed between the opening 14A of the first fluid passage 12A and the opening 14B of the second fluid passage 12B. More particularly, the end portion of each gasket 70, 75 is disposed between the opening 14A of the opening 14A of the first fluid passage 12A and the opening 14B of the second fluid passage 12B.

In the illustrated embodiment, the gaskets 70, 75 have a cylinder shape. In other embodiments, the gaskets 70, 75 may have different shape. For example, the first gasket 70 in an embodiment may have an O-ring shape.

The coupling of the first connector 10A and the second connector 10B includes moving the connectors 10A, 10B closer together to engage their corresponding retaining features (e.g., moving the first connector 10A in direction $D_2$ in FIG. 3, moving the second connector 10B in the direction $D_3$ in FIG. 3, and the like). The coupling of the first connector 10A and the second connector 10B compresses the first gasket 70 and the second gasket 75 between the first connector 10A and the second connector 10B. The coupling of the connectors 10A, 10B pushes the first gasket 70 against the second gasket 75 and compresses the gaskets 70, 75. The first gasket 70 is compressed between the first connector 10A and the second gasket 75. The second gasket 75 is compressed between the second connector 10B and the first gasket 70.

As shown in FIG. 3, the compressed gaskets 70, 75 form a channel 42 that fluidly connects the first fluid passage 12A to the second fluid passage 12B in a sealed manner. The compression of the gaskets 70, 75 against each other and the connectors 10A, 10B provides a sealed connection between the first and second fluid passages 12A, 12B. The coupling of the connectors 10A, 10B as shown in FIG. 3, connects the first fluid passage 12A with the second fluid passage 12B to form a sealed fluid connection that extends through the coupled connectors 10A, 10B. In an embodiment, fluid can then flow through the sealed fluid connection formed in the assembled coupler assembly 1 as shown by the dashed arrow in FIG. 3. For example, the opening 16A of the first fluid passage 12A acts as the inlet for the sealed fluid connection while the opening 16B of the second fluid passage 12B acts as the outlet for the sealed fluid connection.

Figure 4:
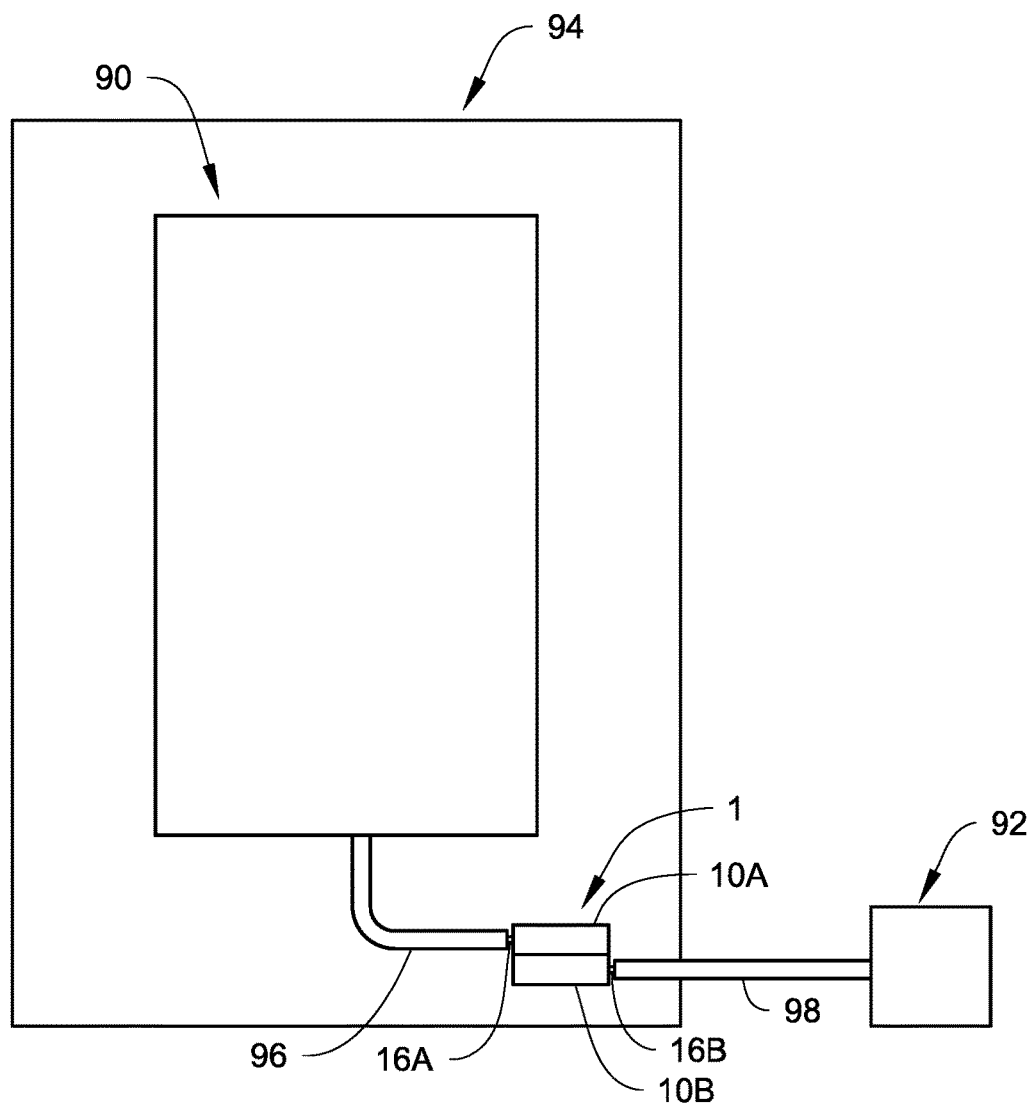
FIG. 4 is a schematic diagram of an embodiment of a low-temperature storage container aseptically connected to a processing device with an assembled aseptic low-temperature coupling assembly.

FIG. 4 is a schematic diagram of a bioprocessing bag 90 aseptically connected to a processing device 92 using the assembled aseptic low-temperature coupling assembly 1. For example, the processing equipment 92 can include equipment that supplies the process material or reactants that form the process material to the fill the bag 90 and/or equipment that utilizes the process material stored within the bioprocessing bag 90. Bioprocessing bag 90 is an example of a low-temperature fluid storage container. An inlet of the assembly 1 (e.g., opening 16A of the first connector 10A) is fluidly connected to the bioprocessing bag 90 and the outlet 2 (e.g., opening 16B of the second connector 10B) is fluidly connected to the processing equipment 92. For example, the inlet of the assembly 1 is configured to be inserted into tubing 96 that connects to the bioprocessing bag 90, and the outlet of the assembly 1 is configured to be inserted into tubing 98 that connects to the processing equipment 92. In another embodiment, the inlet of assembly 1 (e.g., opening 16A of the first connector 10A) may be configured to be directly attached (e.g., molded, fused, or the like) to the bioprocessing bag 90.

The filled bioprocessing bag 90 is configured to be stored at frozen temperatures (e.g., temperatures of less than 0° C.). For example, the bag holder 94 can be configured to hold the bioprocessing bag 90 within a freezing system (e.g., a blast chiller, low temperature freezer, or the like). In an embodiment, the bioprocessing bag 90 is configured to be stored at a temperature of −50° C. or lower. In an embodiment, the bioprocessing bag 90 is configured to be stored at cryogenic temperatures of −150° C. or lower. In an embodiment, the bioprocessing bag 90 is configured to be stored at cryogenic temperatures of −190° C. or lower. As shown in FIG. 4, the first connector 10A and the second connector 10B are configured so as to be disposable within the bag holder 94 along with the bag 90. For example, the first connector 10A is configured to be disposed in bag holder 94 along with the bag 90 during freezing.

The assembly 1 is configured to form a sealed connection after being frozen and then heated back to ambient temperature with the bioprocessing bag 90. For example, the assembly 1 is configured to provide a sealed connection after being frozen to the storage temperature of the bag 90 and then being heated (e.g., applying heat to the bioprocessing bag 90, exposing the bioprocessing bag 90 to ambient temperature, or the like). The first connector 10A after being frozen with the bioprocessing bag 90 and then being heated back to above freezing (e.g., to ambient temperature) is connected with the second connector 10B to form the sealed connection. In an embodiment, the second connector 10B is not frozen with the first connector 10A and the bag 90. For example, ambient temperature is at or about 20° C. The first connector 10A, the second connector 10B, and the gaskets 70, 75 are formed to have no substantial deformation after being cooled to at least −50° C. then heated to ambient temperature. Substantial deformation includes, for example, visible cracking in the material, a shrinkage or expansion relative to its original shape at ambient temperature that can interfere with the connection of first connector 10A to second connection 10B or adversely affect sealing of said connection. The gaskets 70, 75 are each formed to have no substantial deformation by being made of a material that does remains elastic when cooled even to temperatures such as liquid nitrogen temperatures. In embodiments, suitable gaskets showing no substantial deformation at low temperatures can be determined by testing including, as non-limiting examples, temperature retraction testing and/or brittleness testing. Temperature retraction testing can be performed according to ASTM D1329, ISO 2921, or any other suitable testing methodology for determining suitable retraction properties of the material at temperatures where the gasket may be used. Brittleness testing can be performed according to ASTM D2137, ISO 28702, or any other suitable testing methodology for determining resistance to cracking at temperatures where the gasket may be used.

The first connector 10A and its attached pull film 20A and the second connector 10B and its attached second pull film 20B are each formed to have no substantial deformation after returning to ambient temperature from a temperature of −50° C. or lower. The connectors 10A, 10B and the pull films 20A are each formed of polymer material that does not exhibit any visible cracking and maintains the seal of the first opening 14A by the first pull film 20A and the second opening 14B by the second pull film 20B when cooled to a temperature after returning to ambient temperature from a temperature of −50° C. or lower. The connectors 10A, 10B may be made of the same or a different type of polymer material. The pull films 20A, 20B may be made of the same or a different type of polymer material. In an embodiment, each of the first connector 10A and its attached pull film 20A and the second connector 10B and its attached second pull film 20B is formed to have no substantial deformation after returning to ambient temperature from a temperature of −150° C. or lower. In such an embodiment, the connectors 10A, 10B and pull films 20A, 20B are each formed of a polymer material that does not exhibit any visible cracking and maintains the seal of the first opening 14A by the first pull film 20A and the second opening 14B by the second pull film 20B after returning to ambient temperature from a temperature of −150° C. or lower. In an embodiment, the connectors 10A, 10B and pull films 20A, 20B are formed of a polymer material that does not exhibit any substantial deformation after returning to ambient temperature from a temperature of −190° C. or lower. In such an embodiment, the connectors 10A, 10B and pull films 20A, 20B are each formed of a polymer material that does not exhibit any visible cracking and maintains the seal of the first opening 14A by the first pull film 20A and the second opening 14B by the second pull film 20B after returning to ambient temperature from a temperature of −190° C. or lower. For example, this can allow the assembly 1 to be used in cryogenic storage temperatures.

The polymer material(s) of the connectors 10A, 10B is a generally polymer that is generally non-reactive (e.g., non-reactive with air, non-reactive with the process material or the reactants used in a bioprocessing bag). For example, each of the connectors 10A, 10B in an embodiment comprise a fluoropolymer. The polymer material(s) of the connectors 10A, 10B has rigidity at ambient temperature sufficient for compressing the gaskets 70, 75 between the connectors 10A, 10B to form the sealed connection between the fluid pathways 12A, 12B and preventing accidental disengagement of the engaged first and second retaining features.

The polymer material(s) of the pull films 20A, 20B is a generally polymer that is generally non-reactive (e.g., non-reactive with air, non-reactive with process material or reactants used in a bioprocessing bag). The polymer material of the gaskets 70, 75 at ambient temperature has compressibility that causes the gasket(s) 70, 75 when compressed between the connectors 10A, 10B to form the sealed connection between the fluid pathways 12A, 12B. For example, the gaskets 70, 75 in an embodiment comprise one or more of silicone and ethylene-vinyl acetate (EVA).

Figure 5:
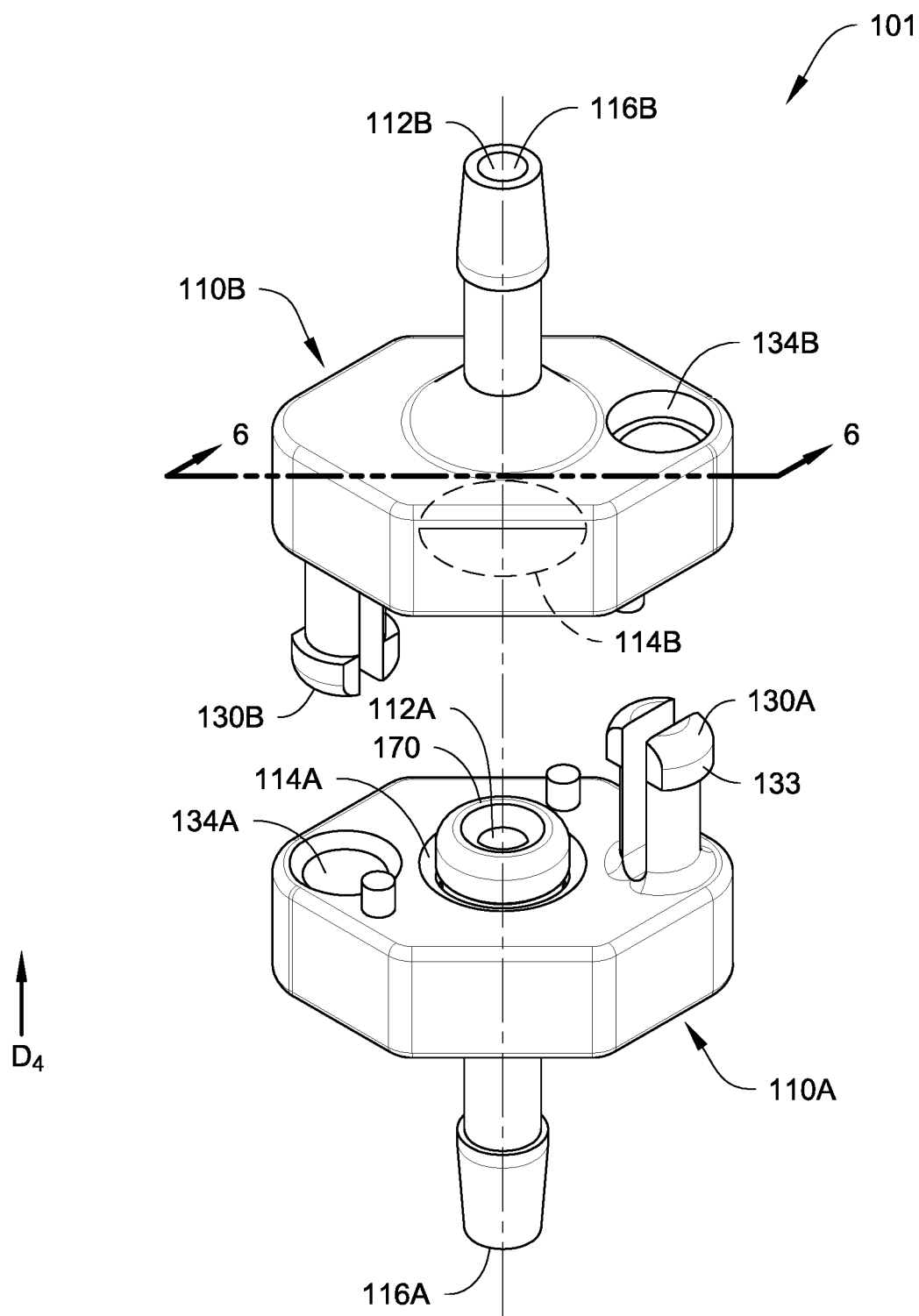
FIG. 5 is a front perspective view of a second embodiment of an aseptic low-temperature coupling assembly.

FIG. 5 is a perspective view of another embodiment of an aseptic low-temperature coupling assembly 101. The coupling assembly 101 includes a first connector 110A and a second connector 110B that couple together to form a sealed fluid connection. The first connector 110A includes a first fluid passage 112A that extends through the first connector 110A. The second connector 110B includes a second fluid passage 112B that extends through the second connector 10B. The first fluid passage 112A and the second fluid passage 112B are generally indicated in dashed lines in FIG. 5. The connectors 110A, 110B can be made of a similar material as discussed above for the connectors 10A, 10B of the assembly 1 in FIGS. 1-3.

The coupling assembly 101 includes a pair of pull films (not shown) that are omitted for illustration purposes. A first pull film covers and seals the first fluid passage 112A and the second pull film covers and seals the second fluid passage 112B. The pulls films can be attached to each connector 110A, 110B and cover their respective fluid passage 112A, 112B in a similar manner to the pulls films 20A, 20B as discussed for the assembly 1 in FIG. 1.

Figure 6:
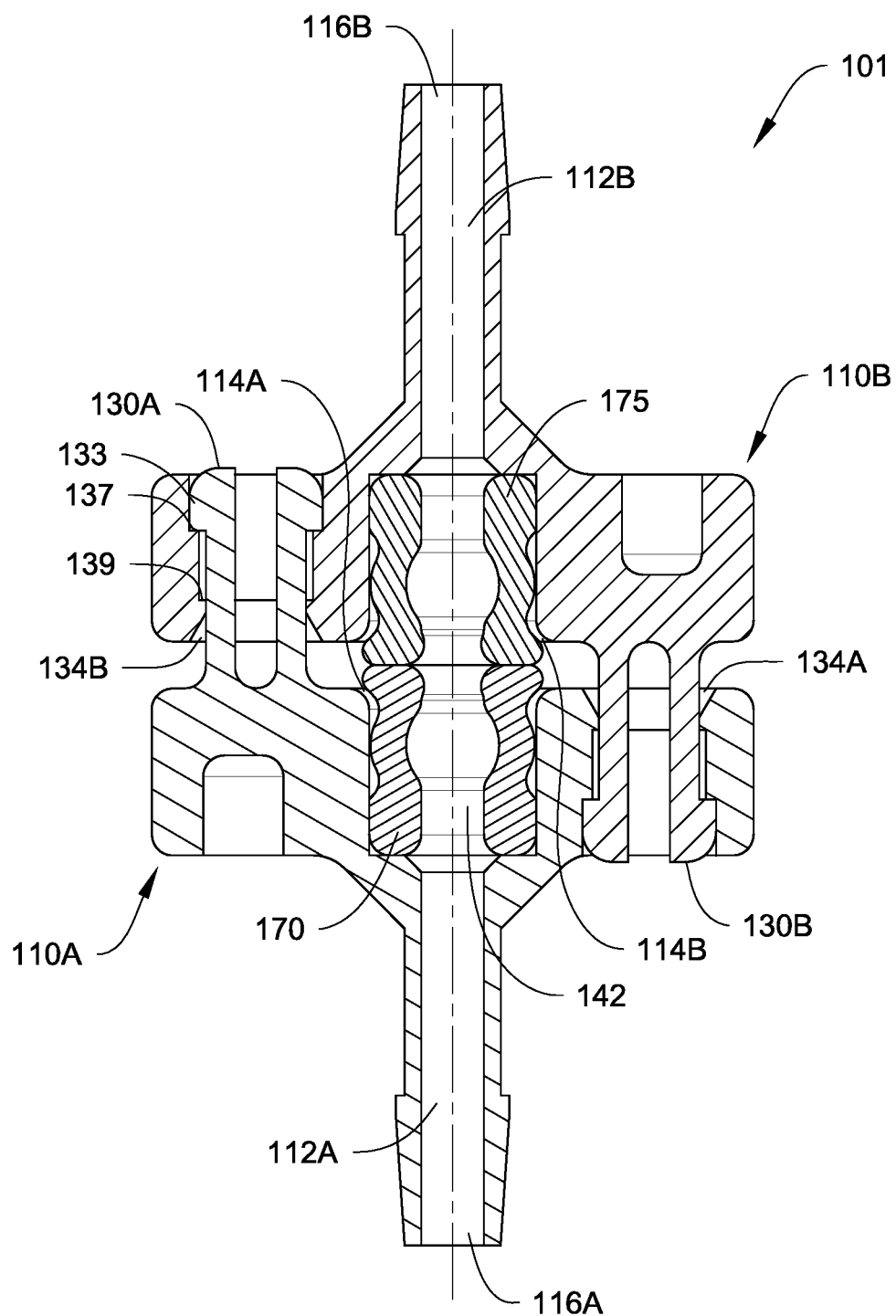
FIG. 6 is a sectional view of the aseptic low-temperature coupling assembly as indicated in FIG. 5, according to an embodiment.

The connectors 110A, 110B include first retaining features 130A, 130B and second retaining features 134A, 134B. Each of the connectors 110A, 110B has at least one of the first retaining features 130A, 130B, and at least one of the second retaining features 134A, 134B. The connectors 110A, 110B are coupled together (e.g., as shown in FIG. 6) by first retaining features 130A, 130B engaging with second retaining features 134A, 134B, as similarly discussed for the connectors 10A, 10B in FIGS. 1-3. The first retaining feature 130A of the first connector 110A engages a corresponding second retaining feature 134B of the second connector 110B, and first retaining feature 130B of the second connector 110B engages corresponding second retaining feature 134A of the first connector 110A. For example, first retaining feature 130A engages with second retaining feature 134B, first retaining feature 130B engages with the second retaining feature 134A.

The first retaining features 130A, 130B can have a structure as similarly discussed above regarding the first retaining features of the connectors 10A, 10B in FIGS. 1-3. The second retaining features 134A, 134B can have a structure as similarly discussed above with respect to the second retaining features of the connectors 10A, 10B in FIGS. 1-3. The first retaining features 130A, 130B engage with corresponding second retaining features 134A, 134B to couple the connectors 110A, 110B together. For example, first retaining feature 130A can include a retaining projection with a tab 133 and second retaining feature 134B can be a retaining slot. As shown in the illustrated embodiment, the first retaining feature 130A on the first connector 110A can include a pair of retaining projections that each include a tab 133. In an embodiment, first retaining feature 130A can include a single retaining projection.

The first connector 110A and the second connector 110B are moved towards each other in a first direction $D_4$ to engage their corresponding retaining features 130A, 130B, 134A, 134B and couple the connectors (e.g., moving the first connector 110A in the direction $D_4$ in FIG. 5, moving the second connector 110B in an opposite direction of direction $D_4$ in FIG. 5). In contrast to the assembly 1 in FIGS. 1-3, movement of the connectors 110A, 110B along a single direction $D_4$ couples the connectors 110A, 110B together.

The first fluid passage 112A includes an opening 114A disposed in the external surface of the first connector 110A. For example, as shown in FIG. 5, the opening 114A is disposed in an upper surface of the first connector 110A that faces the second connector 110B when coupled. The first fluid passage 112A also include a second opening 116A at the opposite end of the first fluid passage 112A. For example, the first opening 114A can be configured to be an inlet of the first connector 110A and the second opening 116A can be configured to be an outlet of the first connector 110A.

The second fluid passage 112B includes an opening 114B disposed in the external surface of the second connector 110B. For example, as shown in FIG. 3, the opening 114B is disposed in a lower surface of the second connector 110B that faces the first connector 110A when coupled. The second fluid passage 112B also include a second opening 116B at the opposite end of the second fluid passage 112B. For example, the first opening 114B can be the inlet of the second fluid passage 112B and the second connector 110B and the second opening 116B can be the outlet of the second fluid passage 112B and the second connector 110B. In the coupled connectors 110A, 110B, opening 116A can be an inlet of the assembly 101 while the opening 116B can be the outlet of the assembly 101.

A first gasket 170 is disposed in the opening 116A of the first fluid passage 112A and a second gasket 175 is disposed in the opening 116B of the second fluid passage 112B. The gaskets 170, 175 can have a similar configuration in the first and second connectors 110A, 110B as discussed above for the gaskets 70, 75 in the first and second connectors 10A, 10B of FIGS. 1-3. The gaskets 170, 175 can be formed of the same material as discussed above for the gaskets 70, 75 in the assembly 1 of FIGS. 1-3.

FIG. 6 is a sectional view of the assembled coupling assembly 101. The sectional view is a horizontal plane along the line indicated in FIG. 5. The coupling of the first connector 110A and the second connector 110B includes moving the connectors 110A, 110B closer together to engage their corresponding retaining features (e.g., moving the first connector 110A in direction $D_4$ in FIG. 5, moving the second connector 110B in the opposite downward in FIG. 5). The coupling of the first connector 110A and the second connector 110B compresses the first gasket 170 and the second gasket 175 between the first connector 110A and the second connector 110B. The coupling of the connectors 110A, 110B pushes the first gasket 170 against the second gasket 175 and compresses the gaskets 170, 175. The first gasket 170 is compressed between the first connector 110A and the second gasket 175. The second gasket 175 is compressed between the second connector 110B and the first gasket 170.

As shown in FIG. 6, the compressed gaskets 170, 175 form a channel 142 that fluidly connects the first fluid passage 112A to the second fluid passage 112B in a sealed manner. The compression of the gaskets 170, 175 against each other and the connectors 110A, 110B provides a sealed connection between the first and second fluid passages 112A, 112B. The coupling of the connectors 110A, 110B as shown in FIG. 6, connects the first fluid passage 112A with the second fluid passage 112B to form a sealed fluid connection that extends through the coupled connectors 110A, 110B. In an embodiment, fluid can then flow through the sealed fluid connection formed in the assembled coupler assembly 101 as shown by the dashed arrow in FIG. 6. For example, the opening 116A of the first fluid passage 112A acts as the inlet for the sealed fluid connection while the opening 116B of the second fluid passage 112B acts as the outlet for the sealed fluid connection.

As shown in the embodiment of FIG. 6, a tab 133 on the retaining projection of first retaining feature 130A forms a snap fit over a lip 137 of the retaining slot of the second retaining feature 134B. The retaining slot can also include multiple lips 137, 139 for engaging with the retaining projection. A first lip 139 is at a first depth in the retaining slot, and the second lip 137 at a second depth in the retaining slot. For example, the first lip 139 may be used to initially couple the first connector 110A to the second connector 110B, and the second lip 137 may be used for compressing the gaskets 70, 75 to the desired compression for the assembled assembly 101. The two retaining projections can be configured to be pushed together to fit into and past the lip 133. For example, the two retaining projections configured to be pinched together to fit into and the past the lip 133.

Figure 7:
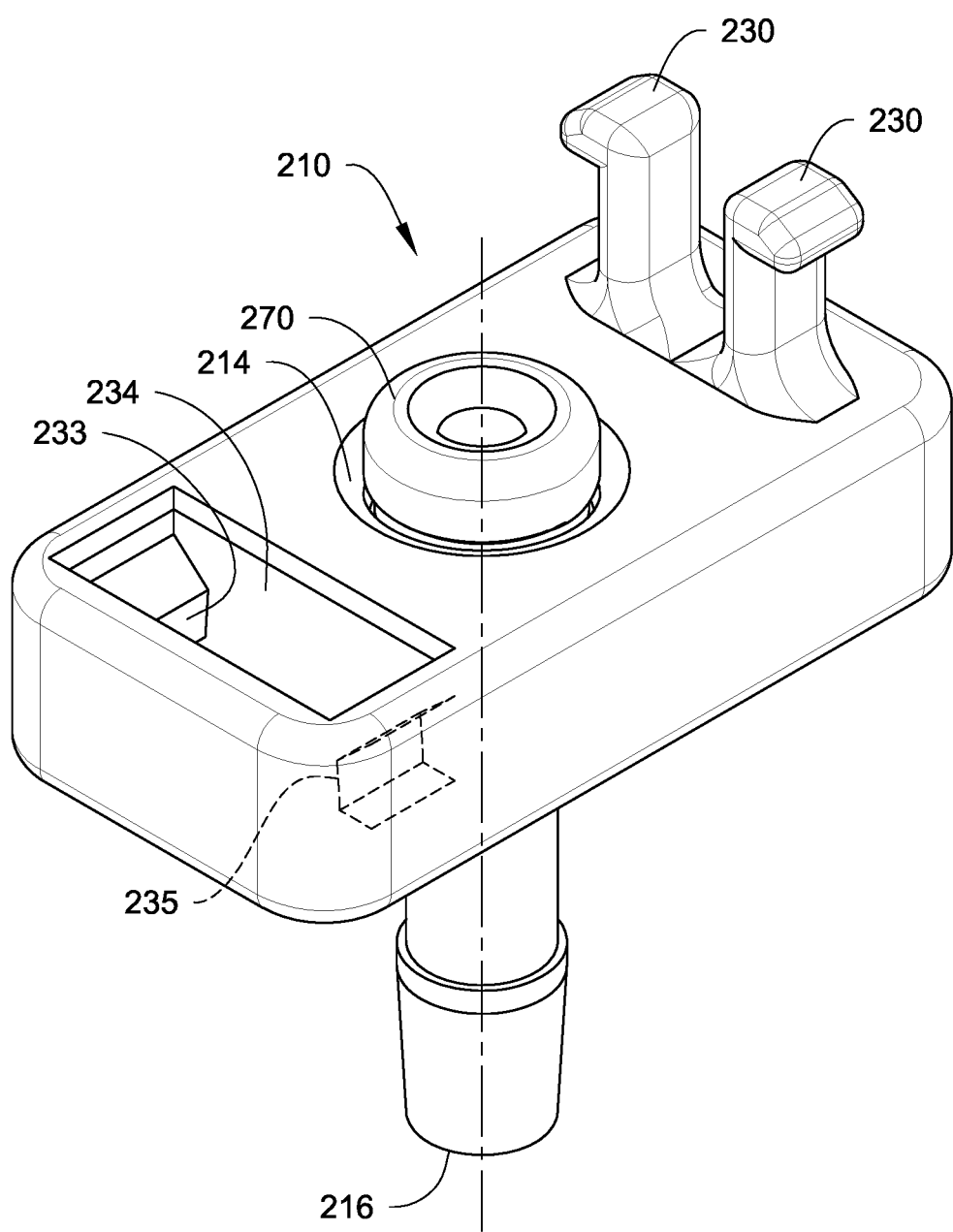
FIG. 7 is an upper perspective view of an embodiment of connector for an aseptic low-temperature coupling assembly.

FIG. 7 is an upper perspective view of a connector 210 for an aseptic low-temperature coupling assembly. An aseptic low-temperature coupling assembly includes two of the connectors 230 which are configured to couple to each other to form a sealed fluid connection, in a generally similar manner to the connectors 10A, 10B of the assembly 1 in FIGS. 1-3 and the connectors of the assembly in FIGS. 5-6.

The connector 210 generally has features similar to the first connector 110A in FIG. 4 except for the configuration of the first retaining feature 230 and the second retaining feature 234. For example, the connector 210 includes a fluid passage 212 (generally indicated in dashed lines in FIG. 7) that extends through the first connector 210 and that includes a first opening 214 and a second opening 216 disposed at an opposite end of the fluid passage 212. A gasket 270 is disposed in the connector 210. For example, the gasket 270 can have a similar configuration in the connector 210 as discussed above for the gasket 70 and the first connector 10A in the assembly 1 of FIGS. 1-3.

The connector 210 includes first retaining feature 230 and second retaining feature 234. The first retaining feature 230 includes two retaining projections and the second retaining feature 234 includes a retaining slot. The retaining slot including a pair of lips 233, 235 disposed on opposite sides of the retaining slot. The two retaining projections configured to bending closer together to fit past the lips 233, 235 in the opposing connector. For example, the retaining projections are pinched together to fit past the lips 233, 235 in the retaining slot.

Aspects:

Any of aspects 1-15 can be combined with any of aspects 16-18.

Aspect 1. An aseptic low-temperature coupling assembly, comprising: a first connector including a first fluid passage extending through the first connector, the first fluid passage including an opening; a second connector including a second fluid passage extending through the second connector, the second fluid passage including an opening, the first connector and the second connector each including a first retaining feature and a second retaining feature, disposed on opposite sides of the opening in the respective one of the first connector and the second connector, wherein the first retaining feature and the second retaining feature have complementary shapes, and a first gasket disposed in one of the first connector and the second connector, wherein the first connector and the second connector are configured to be coupled together by the first and second retaining features of the first connector engaging with the first and second retaining features of the second connector, in which the opening of the first fluid passage aligns with the opening of the second fluid passage, and the first gasket are formed to have no substantial deformation after being cooled to at least −50° C. then heated to ambient temperature.

Aspect 2. The aseptic low-temperature coupling assembly of Aspect 1, wherein the coupling of the first connector and the second connector compresses the first gasket between the first connector and the second connector, in which the first gasket is disposed between the opening of the first fluid passage and the opening of the second fluid passage.

Aspect 3. The aseptic low-temperature coupling assembly of any one of Aspects 1 and 2, further comprising: a first removable film disposed over and sealing the opening of the first fluid passage; and a second removable film disposed over and sealing the opening of the second fluid passage.

Aspect 4. The aseptic low-temperature coupling assembly of Aspect 3, wherein in the coupling of the first connector and the second connector, the first removable film and the second removable film are compressed between the first connector and the second connector, and the first removable film and the second removable film configured to be removable while compressed between the first connector and the second connector.

Aspect 5. The aseptic low-temperature coupling assembly of any one of Aspects 1-4, further comprising: a second gasket disposed in the second connector, the first gasket being disposed in the first connector, wherein the coupling of the first connector and the second connector pushes the first gasket against the second gasket and compresses both the first gasket and the second gasket between the first connector and the second connector.

Aspect 6. The aseptic low-temperature coupling assembly of any one of aspects of 1-5, wherein the first retaining features include a first retaining projection and a second retaining projection, the second retaining features include a first retaining slot and a second retaining slot, the first retaining projection being inserted into the first retaining slot and the second retaining projection being inserted into the second retaining slot to couple the first connector and the second connector.

Aspect 7. The aseptic low-temperature coupling assembly of Aspect 6, wherein the first connector includes the first retaining projection and the first retaining slot, and the second connector includes the second retaining projection and the second retaining slot.

Aspect 8. The aseptic low-temperature coupling assembly of any one of Aspects 6 and 7, wherein the first retaining projection and the second retaining projection have the same shape.

Aspect 9. The aseptic low-temperature coupling assembly of any one of Aspects 1-8, wherein the first connector is formed of a polymer material that does not have substantial deformation after being cooled to at least −50° C. then heated back to the ambient temperature.

Aspect 10. The aseptic low-temperature coupling assembly of any one of Aspects 1-9, wherein the first connector is formed of a polymer material that does not exhibit cracking and maintains a seal after being cooled to at least −190° C. then heated back to the ambient temperature.

Aspect 11. The aseptic low-temperature coupling assembly of any one of Aspects 1-10, wherein the first connector, the second connector, and the first gasket are configured to provide a sealed fluid connection after being cooled to at least −50° C. then heated back to the ambient temperature.

Aspect 12. The aseptic low-temperature coupling assembly of any one of Aspects 1-1, wherein the first connector comprises fluoropolymer.

Aspect 13. The aseptic low-temperature coupling assembly of any one of Aspects 1-12, wherein the first gasket comprises one or more of silicone and ethylene-vinyl acetate (EVA).

Aspect 14. The aseptic low-temperature coupling assembly of any one of Aspects 1-13, wherein the gasket does not exhibit abnormalities when tested at −190° C. according to method B of ISO Standard 28702.

Aspect 15. The aseptic low-temperature coupling assembly of any one of Aspects 1-15, wherein the first connector and the second connector are configured to couple so as to be disposable within a bag holder along with a bag, the first connector configured to be fluidly connected to the bag.

Aspect 16. A method of aseptically connecting a low-temperature fluid storage container, the method comprising: coupling a first connector to a second connector via first retaining features and second retaining features, a first fluid passage extending through the first connector and a second fluid passage extending through the second connector, the first fluid passage and the second fluidly passage each including an opening, wherein coupling the first connector to the second connector includes: engaging the first retaining features with the second retaining features, the first connector and the second connector each including one of the first retaining features and one of the second retaining features disposed on opposite sides of the opening in the respective one of the first connector and the second connector, compressing a first gasket between the first connector and the second connector, the first gasket disposed in one of the first connector and the second connector, and aligning the opening of the first fluid passage with the opening of the second fluid passage, wherein the first gasket are formed to have no substantial deformation after being heated to ambient temperature from a temperature of at least −50° C.

Aspect 17. The method of Aspect 16, further comprising: compressing, between the first connector and the second connector, each of a first pull film disposed over the outlet of the first fluid passage and a second pull film disposed over the opening of the second fluid passage, simultaneously removing the first pull film and the second pull film compressed between the first connector and the second connector by simultaneously pulling the first pull film and the second pull film in a transverse direction.

Aspect 18. The method of Aspect 17, further comprising: compressing a second gasket between the first connector and the second connector, the first gasket disposed in the first connector, and the second gasket disposed in the second connector, wherein prior to removal, the first pull film is disposed over and seals the first passageway and the first gasket.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

What is claimed is:

1. An aseptic low-temperature coupling assembly, comprising:
   a first connector including a first fluid passage extending through the first connector, the first fluid passage including an opening;
   a second connector including a second fluid passage extending through the second connector, the second fluid passage including an opening, the first connector and the second connector each including a first retaining feature and a second retaining feature, disposed on opposite sides of the opening in the respective one of the first connector and the second connector, wherein the first retaining feature and the second retaining feature have complementary shapes, and
   a first gasket disposed in one of the first connector and the second connector, wherein the first connector and the second connector are configured to be coupled together by the first and second retaining features of the first connector engaging with the first and second retaining features of the second connector, in which the opening of the first fluid passage aligns with the opening of the second fluid passage, and the first gasket is formed to have no substantial deformation after being cooled to at least −50° C. then heated to ambient temperature, wherein the first connector and the second connector are configured to couple so as to be disposable within a bag holder along with a bag, the first connector configured to be fluidly connected to the bag.

2. The aseptic low-temperature coupling assembly of claim 1, wherein the coupling of the first connector and the second connector compresses the first gasket between the first connector and the second connector, in which the first gasket is disposed between the opening of the first fluid passage and the opening of the second fluid passage.

3. The aseptic low-temperature coupling assembly of claim 1, further comprising:
   a first removable film disposed over and sealing the opening of the first fluid passage; and
   a second removable film disposed over and sealing the opening of the second fluid passage.

4. The aseptic low-temperature coupling assembly of claim 3, wherein in the coupling of the first connector and the second connector, the first removable film and the second removable film are compressed between the first connector and the second connector, and
   the first removable film and the second removable film are configured to be removable while compressed between the first connector and the second connector.

5. The aseptic low-temperature coupling assembly of claim 1, further comprising:
   a second gasket disposed in the second connector, the first gasket being disposed in the first connector, wherein the coupling of the first connector and the second connector pushes the first gasket against the second gasket and compresses both the first gasket and the second gasket between the first connector and the second connector.

6. The aseptic low-temperature coupling assembly of claim 1, wherein the first retaining features include a first retaining projection and a second retaining projection, the second retaining features include a first retaining slot and a second retaining slot, the first retaining projection being inserted into the first retaining slot and the second retaining projection being inserted into the second retaining slot to couple the first connector and the second connector.

7. The aseptic low-temperature coupling assembly of claim 6, wherein the first connector includes the first retaining projection and the first retaining slot, and the second connector includes the second retaining projection and the second retaining slot.

8. The aseptic low-temperature coupling assembly of claim 6, wherein the first retaining projection and the second retaining projection have a same shape.

9. The aseptic low-temperature coupling assembly of claim 1, wherein the first connector is formed of a polymer material that does not have substantial deformation after being cooled to at least −50° C. then heated back to the ambient temperature.

10. The aseptic low-temperature coupling assembly of claim 1, wherein the first connector is formed of a polymer material that does not exhibit cracking and maintains a seal after being cooled to at least −190° C. then heated back to the ambient temperature.

11. The aseptic low-temperature coupling assembly of claim 1, wherein the first connector, the second connector, and the first gasket are configured to provide a sealed fluid connection after being cooled to at least −50° C. then heated back to the ambient temperature.

12. The aseptic low-temperature coupling assembly of claim 1, wherein the first connector comprises fluoropolymer.

13. The aseptic low-temperature coupling assembly of claim 1, wherein the first gasket comprises one or more of silicone and ethylene-vinyl acetate (EVA).

14. The aseptic low-temperature coupling assembly of claim 1, wherein the first gasket does not exhibit abnormalities when tested at −190° C. according to method B of ISO Standard 28702.

15. A method of aseptically connecting a low-temperature fluid storage container, the method comprising:
   coupling a first connector to a second connector via first retaining features and second retaining features, a first fluid passage extending through the first connector and a second fluid passage extending through the second connector, the first fluid passage and the second fluid passage each including an opening, wherein coupling the first connector to the second connector includes:
   engaging the first retaining features with the second retaining features, the first connector and the second connector each including one of the first retaining features and one of the second retaining features disposed on opposite sides of the opening in the respective one of the first connector and the second connector,
   compressing a first gasket between the first connector and the second connector, the first gasket disposed in one of the first connector and the second connector, and
   aligning the opening of the first fluid passage with the opening of the second fluid passage, wherein
   the first gasket is formed to have no substantial deformation after being heated to ambient temperature from a temperature of at least −50° C., wherein the low-temperature fluid storage container comprises a bag within a bag holder, wherein the first connector and the second connector are configured to couple so as to be disposable within the bag holder along with the bag, the first connector configured to be fluidly connected to the bag.

16. The method of claim 15, further comprising:
   compressing, between the first connector and the second connector, each of a first pull film disposed over the opening of the first fluid passage and a second pull film disposed over the opening of the second fluid passage,
   simultaneously removing the first pull film and the second pull film compressed between the first connector and the second connector by simultaneously pulling the first pull film and the second pull film in a transverse direction.

17. The method of claim 16, further comprising:
   compressing a second gasket between the first connector and the second connector, the first gasket disposed in the first connector, and the second gasket disposed in the second connector, wherein
   prior to removal, the first pull film is disposed over and seals the first passageway and the first gasket.

* * * * *